(12) United States Patent
Walsh et al.

(10) Patent No.: US 6,207,195 B1
(45) Date of Patent: Mar. 27, 2001

(54) THERAPEUTIC NANOSPHERES

(75) Inventors: Scott Walsh, Owings Mills; Ronald Rubenstein; Pam Zeitlin, both of Baltimore; Kam W. Leong, Ellicot City, all of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/095,882

(22) Filed: Jun. 11, 1998

Related U.S. Application Data

(60) Provisional application No. 60/049,497, filed on Jun. 13, 1997.

(51) Int. Cl.[7] .............................. C12N 15/00; A61K 9/14
(52) U.S. Cl. ...................... 424/489; 435/320.1; 435/325; 435/455; 435/458; 514/44
(58) Field of Search ................. 514/44, 963; 424/501, 424/451, 462, 489, 497, 78.08, 491, 492; 435/320.1, 455, 72; 536/23.1, 23.5, 24.1

(56) References Cited

FOREIGN PATENT DOCUMENTS

| | | |
|---|---|---|
| 94/04671 | 3/1994 | (WO) . |
| 96/29998 | 10/1996 | (WO) . |
| 97/46588 | 12/1997 | (WO) . |

OTHER PUBLICATIONS

S.M. Walsh et al. "Combination fo Drug and Gene Delivery by Gelatin Nanospheres for the Treatment of Cystic Fibrosis" Proceedings of the 24th International Symposium on Controlled Release of Bioactive Materials, Stockhom, Jun. 14, 19, 1997, pp. 75–76.

R.C. Rubenstein et al. "In vitro pharmacologic restoration of CFTR–mediated chloride transport with sodium 4–phenylbutyrate in cystic fibrosis epithelial cells containing delta. F508–CFTR" J. Clin. Invest., vol. 100, No. 10, Nov. 15, 1997, pp. 2457–2465.

H. Koy et al. "The Cystic Fibrosis Transmembrane Conductance Regulator Overexpression, Purification, and Characterization of Wild Type and Delta F508 Mutant Forms of the First Nucleotide Binding Fold in Fusion with the Maltose–Binding Protein" J. Biol. Chem., vol. 268, No. 32, Nov. 15, 1993, pp. 24330–24338.

H.L. Newmark et al., "Butyrate as a Differentiating Agent: Pharmacokinetics, Analogues and Current Status" Cancer Letters, vol. 78, 1994, pp. 1–5.

H.Q Mao et al. "DNA–Chitosan Nanospheres for Gene Delivery" Proceedings of the International Symposium on Controlled Release Bioactivee Materials, Jul. 7, 1996, pp. 401–402.

V.L. Truoung et al. "A Target–Specific Microspheres Drug Delivery System Made of Enzymatically Degradeable Gelatin and Chondroitin Sulfate Coacervates" Proceedings of the International Symposium on Controlled Release Bioactive Materials, vol. 20, Jul. 25, 1993 pp. 474–475.

X. Gallet et al. "Prediction of the Antigenic Sites of the Cystic Fibrosis Transmembrane Conductance Regulator Protein by Molecular Modelling" Protein Engineering, vol. 8, No. 8, Aug. 1, 1995, pp. 829–834.

J. Zabner et al. "Repeat Administration of an Denovirus Vector Encoding Cystic Fibrosis Transmembrane Conductance Regulator to the Nasal Epithelium of Patients with Cystic Fibrosis" Journal of Clinical Invstigation, vol. 97, No. 6, Mar. 15, 1996, pp. 1504–1511.

Anderson WF, Nature 392:25–30, 1998.*
Verma et al Nature 389:239–242, 1997.*
Touchette, Nat. Med. 2(1) 7–8, 1996.*
Boucher, J. Clin. Invest. 10(4):441–445, 1999.*
Davis SS, TIBTECH 15:217–224, 1997.*
Leong et al, J. Cont. Rel. 53:183–193, 1998.*
Kay et al, PNAS 94:12744–76, 1997.*
Fahraeus et al J. Pathol. 187:138–146, 1999.*
Collins et al, Blood 85(1):43–49, 1995.*

\* cited by examiner

*Primary Examiner*—John L. LeGuyader
*Assistant Examiner*—Sumesh Kaushal
(74) *Attorney, Agent, or Firm*—Banner & Witcoff, Ltd.

(57) ABSTRACT

4-Phenylbutyrate exerts many beneficial biological effects. It appears to induce the transcription of certain promoters, as well as having a remedial effect on proteins which are aberrantly localized within the cell. In addition, it appears to cause cells to developmentally differentiate. The present invention provides nanosphere formulations of 4-phenylbutyrate and other drugs which remediate defective protein localization intracellularly. These formulations permit lower concentrations of drugs to be administered, providing both cost and safety benefits.

19 Claims, 2 Drawing Sheets

THERAPEUTIC NANOSPHERES

The instant application claims the benefit of Provisional Application Ser. No. 60/049,497, filed Jun. 13, 1997.

TECHNICAL FIELD OF THE INVENTION

This invention is related to the delivery of drugs and genes to cells via nanoparticles.

BACKGROUND OF THE INVENTION

Cystic Fibrosis (CF) is a single gene, recessive disorder characterized by a defective cAMP stimulated chloride conductance across epithelia surfaces, especially in the lung and pancreatic duct. Clinically, this defect results in decreased mucocilliary clearance in lung airways, leading to chronic bacterial infections and inflammation. As a result, patients have a life expectancy of less than 30 years. Clinical trials have thus far focused on either gene or drug therapies for the pulmonary treatment of cystic fibrosis [7,8].

The most common CF mutation, ΔF508, results in failure of the CFTR protein to reach the plasma membrane, likely due to protein trafficking error. The action of 4PBA has been shown to restore CFTR chloride conductance on the plasma membrane of ΔF508 bronchial epithelial cells in vitro [10].

SUMMARY OF THE INVENTION

It is an object of the present invention to provide a solid nanosphere for treating cystic fibrosis.

Another object of the invention is to provide a solid nanosphere for gene delivery.

Another object of the invention is to provide a method of treating cystic fibrosis.

Another object of the invention is to provide a method of treating tumors.

Another object of the invention is to provide a method of treating urea cycle disorders.

It is yet another object of the invention to provide methods of treating a β-hemoglobinopathy.

These and other objects of the invention are achieved by one or more embodiments of the invention. In one embodiment of the invention a solid nanosphere for treating cystic fibrosis is provided. The nanosphere comprises sodium 4-phenylbutyrate (4-PBA).

In another embodiment of the invention a solid nanosphere is provided for treating cystic fibrosis. The nanosphere comprises:
 a wild-type CFTR-encoding nucleic acid; and
 a drug which activates ΔF508 mutant CFTR proteins.

In still another embodiment of the invention a solid nanosphere is provided for gene delivery. The nanosphere comprises:
 sodium 4-phenylbutyrate (4-PBA) and a nucleic acid construct, wherein the construct comprises a promoter operatively linked to a gene coding sequence, wherein the promoter is 4-PBA-inducible.

In yet another embodiment of the invention a method of treating cystic fibrosis is provided. The method comprises the step of:
 administering an aerosolized medicament to a lung of a cystic fibrosis patient wherein the medicament comprises a solid nanosphere comprising 4-PBA.

In still another embodiment of the invention a method of treating tumors is provided. The method comprises the step of:
 administering a medicament to a tumor, wherein the medicament comprises a solid nanosphere comprising 4-PBA.

According to another aspect of the invention a method of treating a urea cycle disorder is provided. The method comprises the step of:
 administering a medicament to the liver of a patient with a urea cycle disorder, wherein the medicament comprises a solid nanosphere comprising 4-PBA.

According to still another aspect of the invention a method is provided for treating a β-hemoglobinopathy. The method comprises the step of:
 administering a medicament to the bone marrow of a patient with a β-hemoglobinopathy, wherein the medicament comprises a solid nanospher 4-PBA.

In still another embodiment of the invention another method is provided for treating a β-hemoglobinopathy. The method comprises the step of:
 administering a medicament to a patient with a β-hemoglobinopathy, wherein the medicament comprises a solid nanosphere comprising 4-PBA.

The invention thus provides the art with formulations and methods for treating a variety of human diseases, including cystic fibrosis, urea cycle disorders, cancers, and β-hemoglobinopathies.

DETAILED DESCRIPTION

Figure 1:
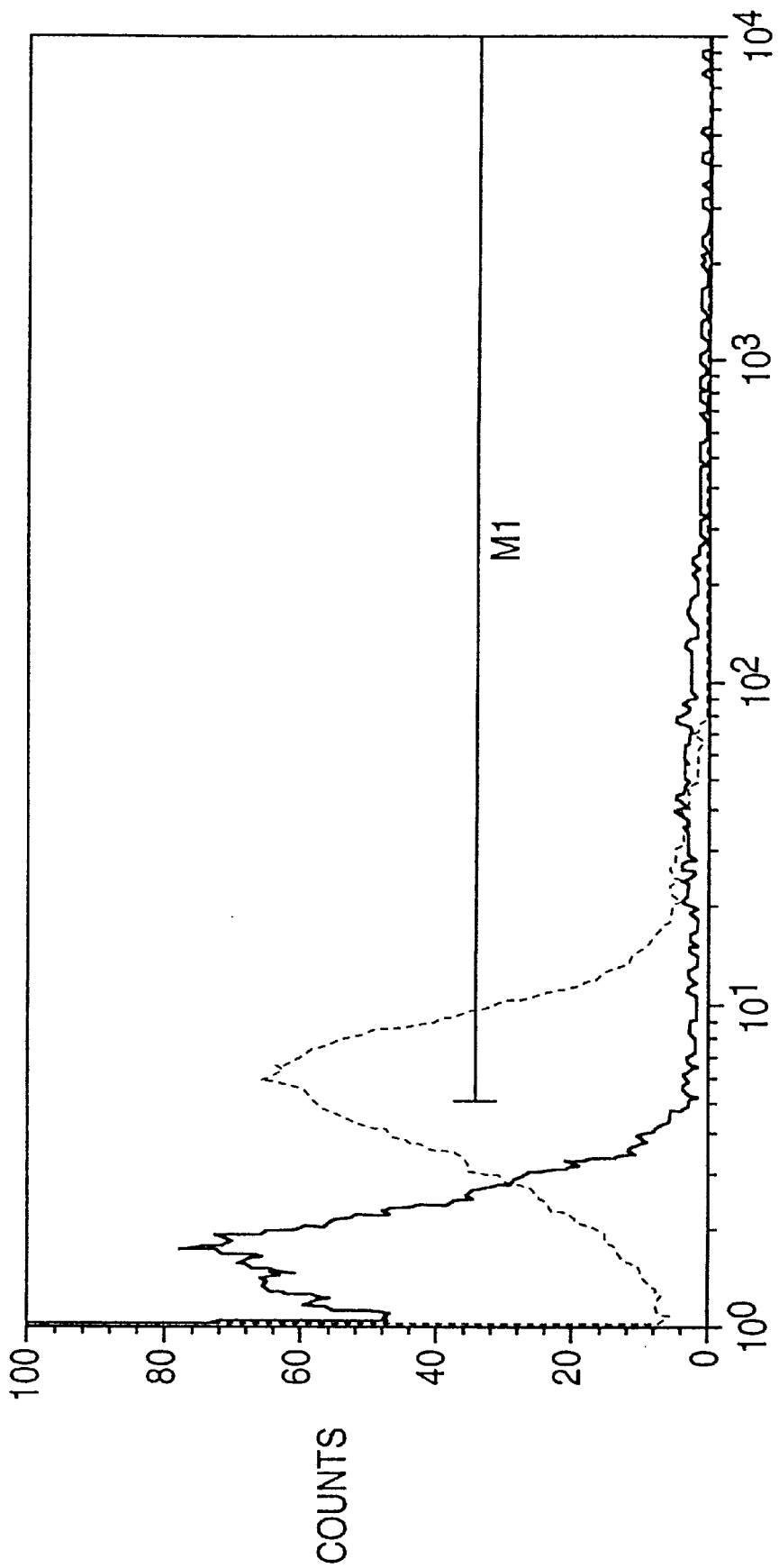
FIG. 1 depicts a flow cytometry histogram of airway epithelial cells transfected with a gene encoding green fluorescent protein. Fluorescent intensity is measured for control (solid-LUL) and nanosphere (dotted-RLL) treated airways. Cells inside the gate M1 are counted as positive for LUL and RLL.

It is the discovery of the present inventors that nanospheres are excellent delivery vehicles for drugs such as 4-phenylbutyrate (4-PBA). Such vehicle formulations permit the use of lower doses, which is both economical and safer. In addition, the delivery of such formulations by inhalation of an aerosol is more palatable than the oral ingestion of higher doses. Such therapy is particularly useful for cystic fibrosis patients.

4-PBA has been found to restore CFTR chloride conductance on the plasma membrane of ΔF508 bronchial epithelial cells in vitro. Use of the present formulations in vivo can restore such function by direct delivery to the bronchial epithelium. Other drugs which have this effect can also be encapsulated by nanospheres. In addition, drugs which have this effect on other CFTR mutants can also be used. Such drugs include milrinone, genistein, 8-cyclopentyl-1,3-dipropyl xanthine (CPX), and 3-isobutyl-1-methyl xanthine (IBMX).

The effect of 4-PBA can be enhanced by including a wild-type CFTR-encoding nucleic acid in the nanosphere. Thus in addition to delivering a drug which enhances the function of mutant CFIR, wild-type CFFR is introduced. A further enhancement occurs if the wild-type coding sequence is introduced in a construct which comprises a promoter which is 4-PBA-inducible. Such inducible promoters include an adeno-associated virus promoter, metallothionine promoter, γ-globin promoter, and the CFTR promoter.

The use of 4-PBA and a construct with a 4-PBA-inducible promoter encapsulated in a nanosphere is not limited to the CFTR gene. Other genes which will have a beneficial therapeutic effect can also be used advantageously. These include without limitation, RB, p53, Bcl2, ADA, γ-globin.

4-PBA also has the effect of inducing cellular differentiation. This is a desirable property in treatment of proliferative disorders, including cancer. Thus nanospheres comprising 4-PBA can be administered to tumors to efficiently deliver a cell-differentiating dose of 4-PBA to the cells. By inducing differentiation, the rapid proliferation of the tumor cells can be abated.

4-PBA has also been used for treating urea cycle disorders. Thus nanospheres comprising 4-PBA can be used for effectively delivering an effective dose of 4-PBA to the target cells which perform the urea cycle.

4-PBA has also been found to induce the expression of fetal hemoglobin in cells which do not express the fetal form. Thus nanospheres comprising 4-PBA can be used to deliver an effective amount to a patient or to isolated bone marrow to induce expression of fetal hemoglobin. This will be of use in the case of β-hemoglobinopathies, such as β-thalassemia and sickle cell anemia.

According to the present invention, gelatin or other polymeric cation having a similar charge density to gelatin, is used to complex with nucleic acids to form nanoparticles. The source of gelatin is not thought to be critical; it can be from bovine, porcine, human, or other animal source. Typically the polymeric cation has a molecular weight of between 19,000–30,000. Poly-L-lysine or chitosan may be particularly useful as the polymeric cation of the present invention. Desirably sodium sulfate is used to induce the coacervation of polymeric cation and nucleic acids. Ethanol can also be used at a concentration of about 40 to 60% to induce coacervation. Other drugs and lysosomolytic agents can be incorporated in the nanoparticle.

Targeting ligands, if desired, can be directly bound to the surface of the nanoparticle or can be indirectly attached using a "bridge" or "spacer". Because of the amino groups provided by the lysine groups of the gelatin, the surface of the nanoparticles can be easily derivatized for the direct coupling of targeting moieties. For example, carbo-diimides can be used as a derivatizing agent. Alternatively, spacers (linking molecules and derivatizing moieties on targeting ligands) such as avidin-biotin and polyethylene glycol can be used to indirectly couple targeting ligands to the nanoparticles. Biotinylated antibodies and/or other biotinylated ligands can be coupled to the avidin-coated nanoparticle surface efficiently because of the high affinity of biotin ($k_a \sim 10^{15}$ $M^{-1}$) for avidin (Hazuda, et al., 1990, Processing of precursor interleukin 1 beta and inflammatory disease, *J. Biol. Chem.*, 265:6318–22; Wilchek, et al., 1990, Introduction to avidin-biotin technology, *Methods In Enzmology*, 184:5–13). Orientation-selective attachment of IgGs can be achieved by biotinylating the antibody at the oligosaccharide groups found on the $F_C$ portion (O'Shannessy, et al., 1984, A novel procedure for labeling immunoglobulins by conjugation to oligosaccharides moieties, *Immunol, Lett.*, 8:273–277). This design helps to preserve the total number of available binding sites and renders the attached antibodies less immunogenic to $F_C$ receptor-bearing cells such as macrophages. Spacers other than the avidin-biotin bridge can also be used, as are known in the art. For example, Staphylococcal protein A can be coated on the nanoparticles for binding the $F_C$ portions of immunoglobulin molecules to the nanoparticles.

Cross-linking of linking molecules or targeting ligands to the nanoparticle is used to promote the stability of the nanoparticle as well as to covalently affix the linking molecule or targeting ligand to the nanoparticle. The degree of cross-linking directly affects the rate of nucleic acids release from the microspheres. Cross-linking can be accomplished using glutaraldehyde, carbodiimides such as EDC (1-ethyl-3-(3-dimethylaminopropyl)-carbodiimide, DCC (N,N'-dicyclohexylcarbodiimide), carboxyls (peptide bond) linkage, DSS (Disuccinimidyl suberate), SPDP (N-succinimidyl 3-[2-pyridyldithio]propionate) bis (sulfosuccinimidyl) suberate, dimethylsuberimidate, etc.

Targeting ligands according to the present invention are any molecules which bind to specific types of cells in the body. These may be any type of molecule for which a cellular receptor exists. Preferably the cellular receptors are expressed on specific cell types only. Examples of targeting ligands which may be used are hormones, antibodies, cell-adhesion molecules, saccharides, drugs, and neurotransmitters.

The nanoparticles of the present invention have good loading properties. Typically, following the method of the present invention, nanoparticles having at least 5% (w/w) nucleic acids can be achieved. Preferably the loading is greater than 10 or 15% nucleic acids. Often nanoparticles of greater than 20 or 30%, but less than 40 or 50% nucleic acids can be achieved. Typically encapsulation efficiencies of nucleic acids into nanoparticles of greater than 95% can be achieved.

The method of the present invention involves the coacervation of polymeric cations and nucleic acids. Because this process depends on the interaction of the positively charged polymeric cations and the negatively charged nucleic acids it can be considered as a complex coacervation process. However, sodium sulfate (or ethanol) induces the coacervation reaction by inducing a phase transition, and therefore it could also be considered as a simple coacervation reaction. Nucleic acids are present in the coacervation mixture at a concentration of between 1 ng/ml to 500 µg/ml. Desirably the nucleic acids are at least about 1–3 kb in length, although smaller molecules can be used. Sodium sulfate is present at between 7 and 43 mM. Gelatin or other polymeric cation is present at between about 2 and 7% in the coacervation mixture.

An attractive nanoparticle delivery system requires a delicate balance among factors such as the simplicity of preparation, cost effectiveness, nucleic acids loading level, controlled release ability, storage stability, and immunogenicity of the components. The gene and drug delivery system described here may offer advantages compared to other particulate delivery systems, including the liposomal system. The problems of instability, low loading level, and controlled release ability are better resolved with the polymeric nanoparticle systems. Gelatin has received increasing biologic use ranging from surgical tissue adhesive (Weinschelbaum, et al., 1992, Surgical treatment of acute type A dissecting aneurysm with preservation of the native aortic valve and use of biologic glue. Follow-up to 6 years, *J. Thorac. Cardiovasc. Surg.*, 130:369–74) to quantitative immunohistochemical assays (Izumi, et al., 1990, Novel gelatin particle agglutination test for serodiagnosis of leprosy in the field, *J. Clinical Microbiol.*, 28:525–9) and as drug delivery vehicle (Tabata, et al., 1991, Effects of recombinant alpha-interferon-gelatin conjugate on in vivo murine tumor cell growth, *Cancer Res.*, 51:5532–8), due to its biocompatibility and enzymatic degradability in vivo. Compared to other synthetic polymeric systems, such as the extensively studied polylactic/polyglycolic copolymers, the mild conditions of nanoparticle formulation are appealing. Unlike the solvent evaporation and hot-melt techniques used to formulate synthetic polymeric nanoparticles, complex coacervation requires neither contact with organic solvents nor heat. It is also particularly suitable for encapsulating bio-macromolecules such as nucleic acids not only through passive solvent capturing but also by direct charge-charge interactions.

Unlike viral vectors, which cannot deliver genes larger than 10 kb, the nanoparticle delivery system of the present invention does not have such size limitations. Nucleic acid molecules of between 1 and 10 kb can be used, between 5 and 15 kb, or between 10 and 50 kb.

In general, the range of possible targets is dependent on the route of injection, e.g., intravenous or intraarterial, subcutaneous, intra-peritoneal, intrathecal, etc. For systemic injections, the specificity of this delivery system is affected by the accessibility of the target to blood borne nanoparticles, which in turn, is affected by the size range of the particles. Size of the particles is affected by temperature, component concentration, and pH in the coacervation mixture. The particles can also be size-fractionated, e.g., by sucrose gradient ultracentrifugation. Particles with size less than 3, 2, or 1 $\mu$m are desirable. Particles less than 150 nanometers can access the interstitial space by traversing through the fenestrations that line most blood vessels walls. Under such circumstances, the range of cells that can be targeted is extensive. An abbreviated list of cells that can be targeted includes the parenchymal cells of the liver sinusoids, the fibroblasts of the connective tissues, the cells in the Islets of Langerhans in the pancreas, the cardiac myocytes, the Chief and parietal cells of the intestine, osteocytes and chondrocytes in the bone, keratinocytes, nerve cells of the peripheral nervous system, epithelial cells of the kidney and lung, etc. The targets for particles with sizes greater than 0.2 microns will be confined largely to the vascular compartment. Here, the targetable cell types include erythrocytes, leukocytes (i.e. monocytes, macrophages, B and T lymphocytes, neutrophils, natural killer cells, progenitor cells, mast cells, eosinophils), platelets, and endothelial cells.

For subcutaneous injections, the targetable cells includes all cells that reside in the connective tissue (e.g., fibroblasts, mast cells, etc.), Langerhans cells, keratinocytes, and muscle cells. For intrathecal injections, the targetable cells include neurons, glial cells, astrocytes, and blood-brain barrier endothelial cells. For intraperitoneal injection, the targetable cells include the macrophages and neutrophil.

Currently 4-PBA is administered for urea cycle disorders as an oral tablet. Twenty grams per day are prescribed. Using the nanoparticle formulations provided herein, dosages can be reduced substantially. Desirable dosages are from 10 to 100 $\mu$g per day, in single or divided doses. However, dosages in the range of 1 $\mu$g to 20 mg can be used.

DNA in nanospheres can be administered in the range of 0.1 mg to 50 mg. If localized administration or targeted nanospheres are used lower amounts of DNA may be used. If systemic administration is used than higher amounts will be desired.

For administration to the lungs, especially for cystic fibrosis, aerosolization is the desired mode of administration. Any device for nebulizing can be used, most conveniently a metered dose inhaler. For treatment of tumors, the nanospheres can be directly administered, for example by injection or implantation. Alternatively, intravenous, intraperitoneal, subcutaneous, or oral administration can be used. If administration is systemic, targeting ligands for the tumor or organ are desirable. For treatment of urea cycle disorders, the nanospheres can be delivered systemically, as described above, or directly to the liver. Bone marrow can be treated ex vivo, and the treated bone marrow can be reinfused into the patient's body. Alternatively, the nanospheres can be administered systemically for treatment of bone marrow in vivo.

Excipients for formulation of the nanospheres of the invention can be any as are known in the art. Typically sterile saline or Ringer's solution will be used.

The above disclosure generally describes the present invention. A more complete understanding can be obtained by reference to the following specific examples which are provided herein for purposes of illustration only, and are not intended to limit the scope of the invention.

EXAMPLE 1

Synthesis of 4-PBA Nanospheres

Gelatin nanospheres are formed when the charge-charge interaction of cationic gelatin and anionic DNA is induced to phase separate from solution. This process depends on several factors: concentration of gelatin and DNA, size and sequence of the plasmid, temperature, mixing speed, and concentration of desolvating agents. Since 4-PBA is a charged molecule in the sodium salt form, it actively participates in the coacervation process and its concentration will affect nanosphere distributions of size, shape, and aggregation. Nanospheres were synthesized with 4-PBA concentrations ranging from 0.1 to 0.5% (w/v) to determine the highest amount of 4-PBA that could be used without compromising the physical quality of the nanospheres. Nanospheres synthesized from 0.1 to 0.4% 4-PBA appeared small, spherical, and totally nonaggregated. However, at concentrations of 4-PBA exceeding 0.4%, the nanospheres started to become larger, somewhat distorted in shape, and mildly aggregated. Therefore, nanospheres made with 0.4% 4-PBA were selected for all of the transfection experiments on IB3 cells.

Nanospheres. A 100 $\mu$L solution of 5% gelatin (pH 5.5) and 5 mM chloroquine diphosphate is mixed with a solution (100 $\mu$L) containing 20 $\mu$g plasmid DNA and 0.1 to 0.5% (w/v) sodium 4-phenylbutyrate (4-PBA) by vortexing. Plain nanospheres are made by replacing the 4-PBA with 4.5 mM $Na_2SO_4$. The reaction is mixed for 20 seconds in a 0.5 mL microcentrifuge tube. Nanospheres are purified from unreacted material by ultracentrifugation into a three level sucrose gradient (30%, 55%, and 88%) at 50,000×g and 25° C. for 8 minutes. The top layer (reaction mixture) is then removed and the nanospheres are resuspended in the sucrose. Human holo-transferrin (0.25 mg/mL; Sigma) and 25 mM 2-[N-Morpholino]ethane-sulfonic acid (MES, pH 4.5) are added to the nanosphere solution and allowed to incubate for 5 min RT. The nanosphere/transferrin solution is crosslinked for 30 minutes at RT with 50 $\mu$g/mL 1-Ethyl-3-[3-dimethylaminopropyl]-carbodiimide Hydrochloride (EDC; Pierce). The reaction is quenched by adding 30 mM sodium acetate (pH 5.5). Sucrose, unconjugated transferrin, and non-encapsulated 4-PBA are removed from the solution by dialysis (300,000 MWCO) overnight against phosphate buffered saline (PBS). The concentration of encapsulated DNA in the solution is measured using a Hoechst dye, H 33258. Nanospheres are digested for two hours in 1.25% trypsin, reacted with the dye, and measured in a DyNA Quant 200 fluorometer (Pharmacia).

EXAMPLE 2
Induction of Endogenous CFTR Expression by 4-PBA Nanospheres

Studies have shown that 4-PBA can induce CFTR expression and cAMP stimulated $Cl^-$ transport in $\Delta$F508 expressing cells. We tested the hypothesis that gelatin nanospheres could deliver a controlled, intracellular dose of 4-PBA to $\Delta$F508 expressing IB3 cells and induce CFTR expression and function. Nanospheres containing 4-PBA were incubated with IB3 cells for four hours at two different doses, 5 or 10 $\mu$g encapsulated DNA. A green fluorescence protein (GFP) reporter gene was used for the plasmid cDNA in order to independently detect the effects of drug and gene therapy [6]. Induction of CFTR expression was detected by anti-CFTR antibody staining, where positive staining was characterized by blue color on the membrane surface of IB3 cells. Doubling the nanosphere dose appeared to increase both the percentage of CFTR expressing cells and the overall intensity of expression. Furthermore, CFTR induction by the nanospheres was more intense than free 4-PBA treated cells, despite exposing the cells to free 4-PBA for all three days whereas nanospheres were only exposed for only four hours.

Although the loading level of 4-PBA in nanospheres has not been measured, a simple thought experiment demonstrates that CFTR induction is nanosphere dependent and not due to nanosphere break-up and consequent 4-PBA release into the culture medium. The loading level of most drugs in nanospheres has been found to be quite low, usually less than 10%. Chloroquine has been measured in gelatin nanospheres at a loading level of 2% with respect to the DNA mass. Therefore, even if we assume a very high loading level of 50% for 4-PBA, the concentration in the culture medium would only amount to 9 and 18 $\mu$M (for the 5 and 10 $\mu$g DNA doses, respectively), which is 50 and 100 times less than concentration in free 4-PBA treated cells. These results strongly indicate that nanospheres can deliver a high local dose of 4-PBA inside cells, thus improving bioavailability of the drug.

Tissue Culture. The human bronchial epithelial cell line, CFBE IB3-1 (IB3 cells), has the genotype $\Delta$F508/W1282X; however, only the $\Delta$F508 is expressed [7, 8]. Cells were grown at 37° C. in 5% $CO_2$ and LHC-8 medium (Biofluids) supplemented with 10% fetal bovine serum. Eighteen hours prior to transfection, IB3 cells were seeded onto coverslips in 6-well culture dishes or 35 mm dishes at a density of 100,000 cells per well. The medium was replaced with transfection media (MEM plus 1% fetal bovine serum) after washing once with PBS. Gelatin nanospheres made with 0.4% 4-PBA were added to wells at a DNA dose of 5 or 10 $\mu$g, which is a typical dose used for gene transfer with these nanospheres. Control wells were either untreated or incubated with 1 mm free 4-PBA. After four hours, the transfection media was removed and replaced with normal IB3 growth medium. Cells were allowed to grow for three days before assaying for CFTR expression. Free 4-PBA treated wells were exposed to the 1 mm concentration (in the growth medium) for the entire three-day period.

Immunohistochemical staining of cells for CFTR protein. B3 cells were washed twice with PBS, fixed for 10 minutes in 10% formalin, and permeabilized for 10 minutes in 95% methanol. The cells were incubated one hour with a 1:500 dilution of antibody 169. This rabbit polyclonal antibody binds to sequences within the R domain, amino acid residues 724–746, of CFTR protein [9]. A horseradish peroxidase (HRP) labeled secondary antibody (1:1000 dilution of donkey antirabbit antibody; Amersham) was then incubated with the cells for one hour. Bound HRP-labeled antibody was detected by TrueBlue™ peroxidase substrate (KPL), which gives a dark blue/purple positive staining. Nuclei were counterstained with Nuclear Fast Red (Digene Diagnostics). Mounted coverslips were examined and photographed under light microscopy. Digitized images were color enhanced using Adobe PhotoShop (v. 4.0). All images were treated with an identical enhancement protocol.

EXAMPLE 3
Induction of Chloride Efflux by 4-PBA Nanospheres

Figure 2A:
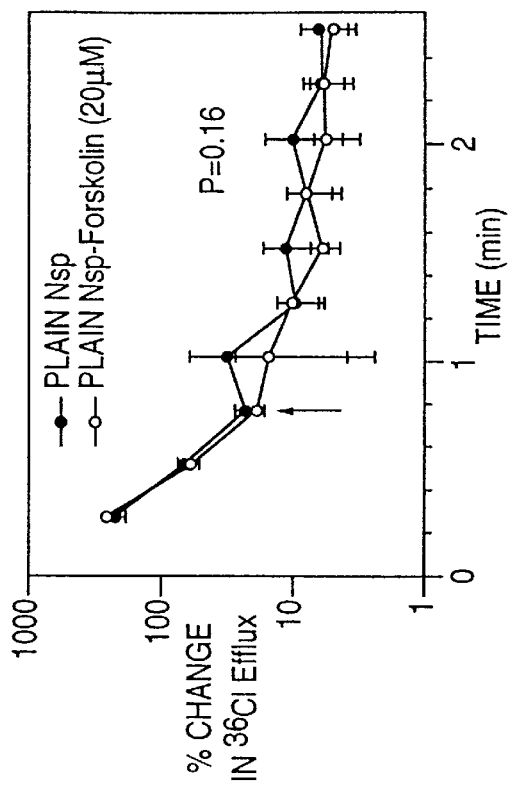
FIGS. 2A–D show efflux of $^{36}Cl^-$ from IB3 cells. Data are plotted as the percent change in chloride efflux over each 15 second interval. Forskolin is added to stimulate cells (open circles) at every time point after 45 seconds (arrows). Unstimulated cells (filled circles) received plain Ringer's solution at every time point. P values are determined by a rank Sum test performed on points from 0:45 to 2:30.
Figure 2B:
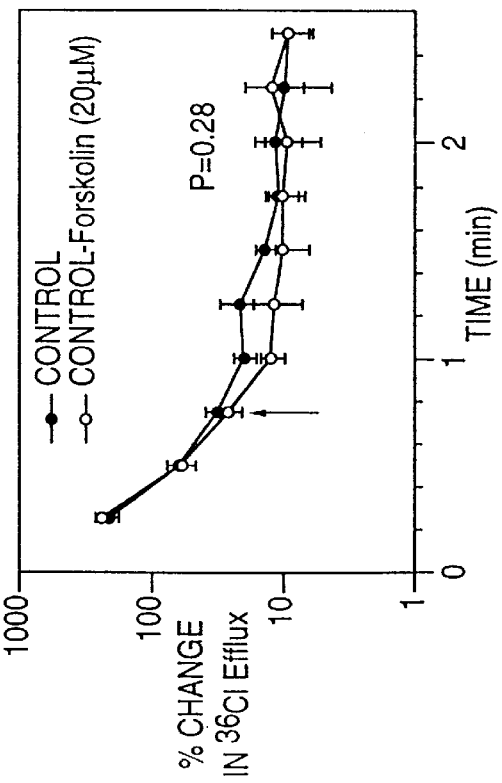
Figure 2C:
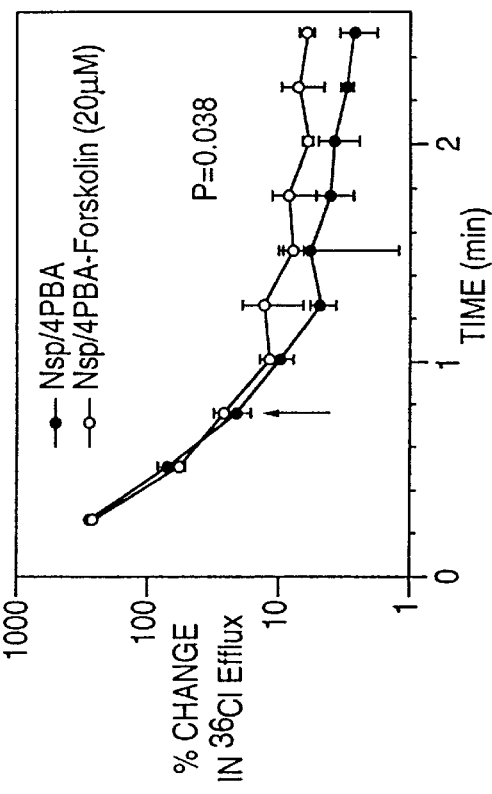
Figure 2D:
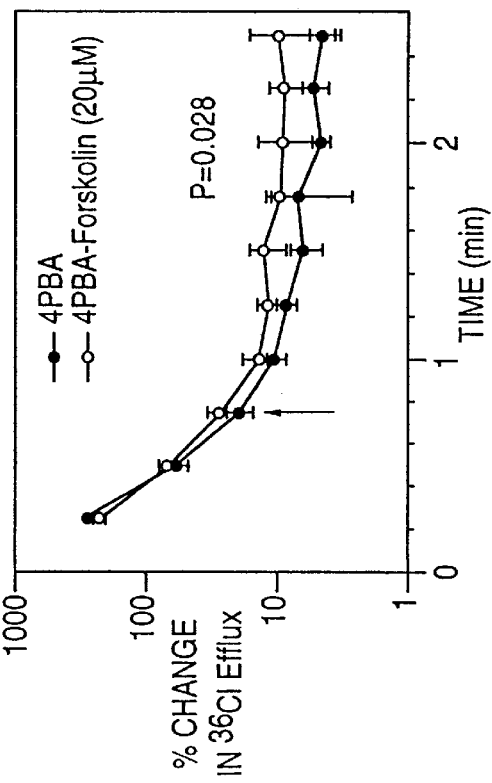

Nanosphere delivered 4-PBA also restores the cAMP stimulated $Cl^-$ transport in IB3 cells (FIGS. 2A–D). Cells treated with 4-PBA nanospheres at a 5 $\mu$g DNA dose show a statistically significant increase in $Cl^-$ efflux upon stimulation with forskolin, a cAMP agonist. Plain nanospheres were used to determine whether any component of the nanosphere other than 4-PBA was responsible for CFTR induction. There was no statistical difference between forskolin stimulated and unstimulated cells incubated with plain nanospheres, showing that 4-PBA alone is responsible for the observed effect. The expression of functional CFTR shown in these results demonstrate that gelatin nanospheres can efficiently deliver a high local dose of 4-PBA for a comparatively small overall drug dose.

Chloride Efflux Assay. Cells were transfected with plain or 4-PBA nanospheres at a DNA dose of 5 $\mu$g per 35 mm dish. Chloride efflux was measured three days post-transfection as previously described [4, 10]. Each dish was incubated with 3 $\mu$Ci of $^{36}Cl^-$ in bicarbonate-free Ringer's balanced salt solution for two hours at 37° C. After loading, the cells were washed three times with 1 mL ice cold Ringer's and once with warm (37° C.) Ringer's. At time 0, 1 mL of warm Ringer's was added, immediately collected, and replace with 1 mL fresh Ringer's. The solution was collected at 15 seconds and replaced with 1 mL fresh Ringer's. This process was repeated every 15 seconds up to 2½ minutes. Finally, 0.2 N NaOH was added to release any remaining $^{36}Cl^-$ in the cells. The radioactivity of each sample was measured by liquid scintillation counting.

EXAMPLE 4
Effect of 4-PBA on Gene Transfection

The ability of gelatin nanospheres encapsulated with 4-PBA to transfect IB3 cells with the GFP cDNA was measured to ensure that 4-PBA does not affect the gene transfer capabilities of nanospheres. Expression of GFP was measured by flow cytometry; nanospheres with 4-PBA showed GFP expression in 3.32% of cells compared to 4.07% for plain (no 4-PBA) nanospheres, demonstrating that gene transfer is unaffected by coencapsulation of 4-PBA. However, the induction of CFTR shows a much higher percentage of positive cells (at least 50%), indicating that although most cells are efficient in nanosphere uptake, only a small percentage express the transferred cDNA.

EXAMPLE 5
In vivo Gene Delivery Using 4-PBA Nanospheres

Delivery of the CFTR gene to rabbit airway epithelia was determined by specifically amplifying the pSA306 DNA without amplification of endogenous rabbit CFTR DNA. This was made possible by choosing one of the PCR primers in the fusion peptide region of pSA306, which is not present in any native CFTR sequence. Rabbits treated with nanospheres showed a strong positive signal for the presence of pSA306 CFTR DNA compared to rabbits treated with a saline control. The DNA was observed in a high percentage of airway epithelial cells and appears to be highly localized to the nucleus, an important step in the expression of any exogenously delivered gene. DNA persisted in airway nuclei for at least 28 days. Histological evaluation of lung sections focused on peribronchial and perivascular polymorphonuclear infiltrates as well as perilymphoid hyperplasia. Rabbits treated with CFTR DNA-gelatin nanospheres were indistinguishable histologically from control animals receiving saline administration, demonstrating the safety of this nonviral delivery system.

Gene expression was evaluated using a GFP reporter gene. Fluorescence of cells brushed from airways of the LUL (control) were compared to brushed cells from RLL (nano-sphere treated) airways by FacScan analysis. GFP expression is detectable in 43% of the brushed airway cells from the RLL compared to the LUL (background fluorescence).

4-PBA nanospheres were successfully synthesized by substituting 0.4% (w/v) 4-PBA for $Na_2SO_4$ as the desolvating agent. The participation of 4-PBA in the coacervation process demonstrates coencapsulation of the drug, although its loading level has yet to be measured. The Dd-UF5 plasmid was substituted for the CFTR gene so that the effects of gene and drug transfer could be studied independently. Transfection levels of 5–10% in IB3-1 cells were observed with these nanospheres, which is comparable to expression obtained with normal DNA-gelatin nanospheres. Therefore, 4-PBA is not interfering with the transfer or expression of cDNA. The effect of encapsulated 4-PBA on stimulated chloride conductance in IB3-1 cells is illustrated in FIGS. 2A–D. 4-PBA nanospheres were capable of restoring cAMP stimulated chloride conductance to levels similar to that achieved in cells treated with free 4-PBA (p values <0.05). Nanospheres without 4-PBA showed no stimulated chloride conductance (p=0.16). These results indicate the feasibility of combinational therapy by a single carrier and suggest a more effective strategy of treating the chloride conductance defect in CF than either gene or drug therapy alone.

Plasmids. Two constructs were used for the detection of in vivo transfection. The pSA306 CFTR plasmid was used for in situ DNA PCR and histological evaluation; it codes for the entire CFTR cDNA sequence, is flanked by the AAV inverted terminal repeats (ITR's), and contains a 26 amino acid fusion peptide at the amino terminus not found in native CFTR (MLLIYVHTKNQHTLIDASELFIRPGT) [4]. A GFP construct, Dd-UF5, driven by RSV and flanked by AAV ITR's was used to evaluate in vivo gene expression [6].

Nanosphere Synthesis. Nanospheres (100–600 nm) for gene transfer were formed by the complex coacervation of 5% porcine gelatin (pH 5.5; with 5 mM chloroquine diphosphate) and DNA (200 μg/mL CFTR cDNA in 4.5 mM $Na^2SO_4$ solution) at 55° C. while stirring at high speed on a vortex mixer. Nanospheres for drug delivery were synthesized similarly except 0.4% (w/v) 4-PBA replaced $Na^2SO_4$ and GFP cDNA replaced CFTR cDNA. The nanospheres were purified by ultracentrifugation on a sucrose gradient. Gelatin crosslinking as well as transferrin (1 mg/mL) conjugation to the surface of the nanospheres was achieved using EDC (0.1 mg/mL) for 45 minutes at room temperature. The crosslinked nanosphere solution was incubated for 24 hours at 4° C. in 0.4 M calcium chloride and purified by dialysis (300,000 MWCO) for 24 hours in Ringer's balanced salt solution (pH 7.4).

In Vivo Delivery of Nanospheres. A 1 mL dose of approximately 1 mg of nanospheres containing 350 μg CFTR cDNA or 100 μg GFP cDNA was administered to the right lower lobe of New Zealand White Rabbits by a pediatric bronchoscope. Control animals received either Ringer's buffer or 350 μg free CFTR DNA. Animals were sacrificed at days 7, 14, and 28 post-transfection. Lung tissue from CFTR treated rabbits were formalin fixed, 5 μM-sectioned, and subjected to in situ PCR amplification for the detection of CFTR DNA (Perkin Elmer). A digoxigenin labeled probe was used to detect the PCR product. Histology sections were evaluated by Fred Askin, a clinical pathologist at Johns Hopkins, for the presence of any immune reaction to the nanospheres. Bronchial epithelia brushings were obtained from the left upper (LUL) and right lower (RLL) lobes of rabbits treated with GFP. These epithelial cells were trypsinized for two hours and measured for expression by flow cytometry (FacScan).

In Vitro Correction of Chloride Transport. IB3-1 cells (Δ508/ΔF508) were treated with 4-PBA/Dd-UF5 nanospheres for 4 hours, replaced with fresh media, and allowed to grow for 3 days. The cells were loaded with $^{36}Cl^-$ (2 μCi) for 2 hours, washed with fresh buffer, then stimulated with forskolin. $^{36}Cl^-$ released into the media at different time points was collected and counted.

REFERENCES

1. Zeitlin, P., et al., A cysticfibrosis bronchial epithelial cell line: immortalization by adeno-12-SV40 infection. Am J Respir Cell Mol Biol, 1991. 4(4): p. 313–9.
2. Zeitlin, P., et al., CFTR protein expression in primary and cultured epithelia. Proc Natl Acad Sci U S A, 1992. 89(1): p. 344–7.
3. Crawford, I., et al., Immunocytochemical localization of the cysticfibrosis gene product CFTR. Proc Natl Acad Sci U S A, 1991. 88(20): p. 9262–6.
4. Flotte, T., et al., Expression of the cystic fibrosis transmembrane conductance regulator from a novel adeno-associated virus promoter. J Biol Chem, 1993. 268(5): p. 3781–90.
5. Egan, M., Schwiebert, E., and Guggino, W., Differential expression of ORCC and CMTR induced by low temperature in CF airway epithelial cells. Am J Physiol, 1995. 268(1 Pt 1): p. C243–51.
6. Zolotukhin, S., Potter, M., Hauswirth, W., Guy, J., and Muzyczka, N., A "humanized" green fluorescent protein cDNA adapted for high-level expression in mammalian cells. J Virol, 1996. 70(7): p. 4646–54.
7. Hay, J. et al. Human Gene Therapy 6:11,1481–96 (1995)
8. Bennet, W. et al. Am J Respir Crit Care Med 153:6 Pt1, 1786–(1996)
9. Walsh, S. et al. Int Symp Control Release Bioact Mater. 23:73–4 (1996)
10. Rubenstein, R. and Zeitlin, P. Pediatric Pulmonary, Suppl. 12:234 (abstract) (1995).

What is claimed is:

1. A solid nanosphere of comprising sodium 4-phenylbutrate (4-PBA) wherein the nanosphere is formed by coacervation of a polycation and a polyanion.

2. The solid nanosphere of claim 1 wherein the polycation is a protein.

3. The solid nanosphere of claim 2 wherein the polycation is gelatin.

4. The solid nanosphere of claim 1 wherein the polycation is a polysaccharide.

5. The solid nanosphere of claim 4 wherein the polycation is chitosan.

6. The solid nanosphere of claim 1 wherein the polyanion is nucleic acids.

7. The solid nanosphere of claim 6 wherein the DNA is wild-type CFTR cDNA.

8. The solid nanosphere of claim 2 wherein a targeting ligand which is capable of binding to a cellular receptor is covalently bound to the nanosphere.

9. A solid nanosphere comprising:

the wild-type CFTR-encoding nucleic acid; and a drug which activates ΔF508 mutant CFTR proteins.

10. A solid nanosphere of claims 9 wherein the drug is 4-PBA.

11. The solid nanosphere of claim 9 wherein the drug is milrinone.

12. The solid nanosphere of claim 9 wherein the drug is genistein.

13. The solid nanosphere of claim 9 wherein the drug is 8-cyclopentyl-1,3-dipropyl xanthine (CPX).

14. The solid nanosphere of claim 9 wherein the drug is. 3-isobutyl-1-methyl xanthine (IBMX).

15. A solid nanosphere comprising:

sodium 4-phenylbutyrate (4-PBA) and a nucleic acid construct, wherein the construct comprises a promoter operatively linked to a gene coding sequence, wherein the promoter is 4-PBA-inducible.

16. A solid nanosphere of claim 15 wherein the promoter is an adeno-associated virus promoter.

17. A solid nanosphere of claim 15 wherein the promoter is a metallothionine promoter.

18. A solid nanosphere of claim 15 wherein the promoter is a γ-globin promoter.

19. A solid nanosphere of claim 15 wherein the promoter is a CFTR promoter.

* * * * *

UNITED STATES PATENT AND TRADEMARK OFFICE
CERTIFICATE OF CORRECTION

PATENT NO.     : 6,207,195 B1                                           Page 1 of 1
DATED          : March 27, 2001
INVENTOR(S)    : Scott Walsh et al.

It is certified that error appears in the above-identified patent and that said Letters Patent is hereby corrected as shown below:

Column 10,
Line 59, "of" has been deleted.

Column 11,
Line 5, "DNA is" has been replace with -- nucleic acids are --.

Signed and Sealed this

Twenty-eighth Day of May, 2002

Attest:

JAMES E. ROGAN
Attesting Officer              Director of the United States Patent and Trademark Office